United States Patent
Vetter et al.

(10) Patent No.: US 6,921,514 B1
(45) Date of Patent: Jul. 26, 2005

(54) DEVICE FOR CARRYING OUT AN ALMOST SIMULTANEOUS SYNTHESIS OF A PLURALITY OF SAMPLES

(75) Inventors: Dirk Vetter, Freiburg (DE); Kristina Schmidt, Heidelberg (DE)

(73) Assignee: Graffinity Pharmaceutical Design GmbH, Heidelberg (DE)

( * ) Notice: Subject to any disclaimer, the term of this patent is extended or adjusted under 35 U.S.C. 154(b) by 0 days.

(21) Appl. No.: 09/720,284

(22) PCT Filed: Jun. 10, 1999

(86) PCT No.: PCT/EP99/04050

§ 371 (c)(1),
(2), (4) Date: Dec. 21, 2000

(87) PCT Pub. No.: WO99/67024

PCT Pub. Date: Dec. 29, 1999

(30) Foreign Application Priority Data

Jun. 23, 1998 (DE) .......................... 198 27 754

(51) Int. Cl.[7] ................................................ B01L 3/00
(52) U.S. Cl. .................... 422/102; 422/99; 422/100; 436/174; 436/180
(58) Field of Search .................... 435/287.7, 287.8, 435/288.3, 288.4; 422/99, 100, 102, 104; 436/174, 179, 180

(56) References Cited

U.S. PATENT DOCUMENTS

| | | | |
|---|---|---|---|
| 5,429,807 A | | 7/1995 | Matson et al. |
| 5,888,834 A | * | 3/1999 | Ishikawa et al. ............ 436/518 |
| 6,051,190 A | * | 4/2000 | Birch et al. .................. 422/100 |
| 6,287,872 B1 | * | 9/2001 | Schurenberg et al. ....... 436/181 |
| 6,303,387 B1 | * | 10/2001 | Birch et al. .................. 436/180 |
| 6,432,358 B2 | * | 8/2002 | Norris et al. ................. 422/58 |
| 6,565,813 B1 | * | 5/2003 | Garyantes .................... 422/102 |
| 6,613,283 B2 | * | 9/2003 | Reo ............................. 422/99 |
| 6,689,323 B2 | * | 2/2004 | Fisher et al. ................ 422/100 |
| 6,692,672 B1 | * | 2/2004 | Deschenes et al. ......... 264/151 |

FOREIGN PATENT DOCUMENTS

| | | |
|---|---|---|
| EP | 0075605 | 4/1983 |
| WO | WO91/17832 | 11/1991 |
| WO | WO97/19749 | 6/1997 |
| WO | WO97/33737 | 9/1997 |
| WO | WO97/37755 | 10/1997 |
| WO | WO97/43629 | 11/1997 |
| WO | WO98/06490 | 2/1998 |
| WO | WO98/15355 | 4/1998 |
| WO | WO98/16315 | 4/1998 |
| WO | WO98/24543 | 6/1998 |

* cited by examiner

*Primary Examiner*—Jill Warden
*Assistant Examiner*—Dwayne K Handy
(74) *Attorney, Agent, or Firm*—Jordan and Hamburg LLP

(57) ABSTRACT

The invention relates to a device for carrying out an almost simultaneous synthesis of a plurality of samples. The device is especially suitable for use in automated laboratory processes in the area of combinatorial chemistry. The aim of the invention is to provide a device of this type which enables the synthesis of a plurality of samples bonded to microbeads, said microbeads being provided in the cavities of a support plate. To this end, a plane support plate (1) is provided with a plurality of cavities (11) arranged regularly in an iterative grid. The cavities accommodate microbeads (12). A removable covering (2) is provided, said covering being provided with webs (21) which each cover at least one of a row of associated cavities (11) in such a way that a capillary gap (3) is formed between the microbeads (12) and the webs (21) and larger recesses (22) are left respectively between the adjacent webs (21). A dosed liquid dispenser (4) is allocated to each capillary gap (3).

8 Claims, 4 Drawing Sheets

Figure 1:
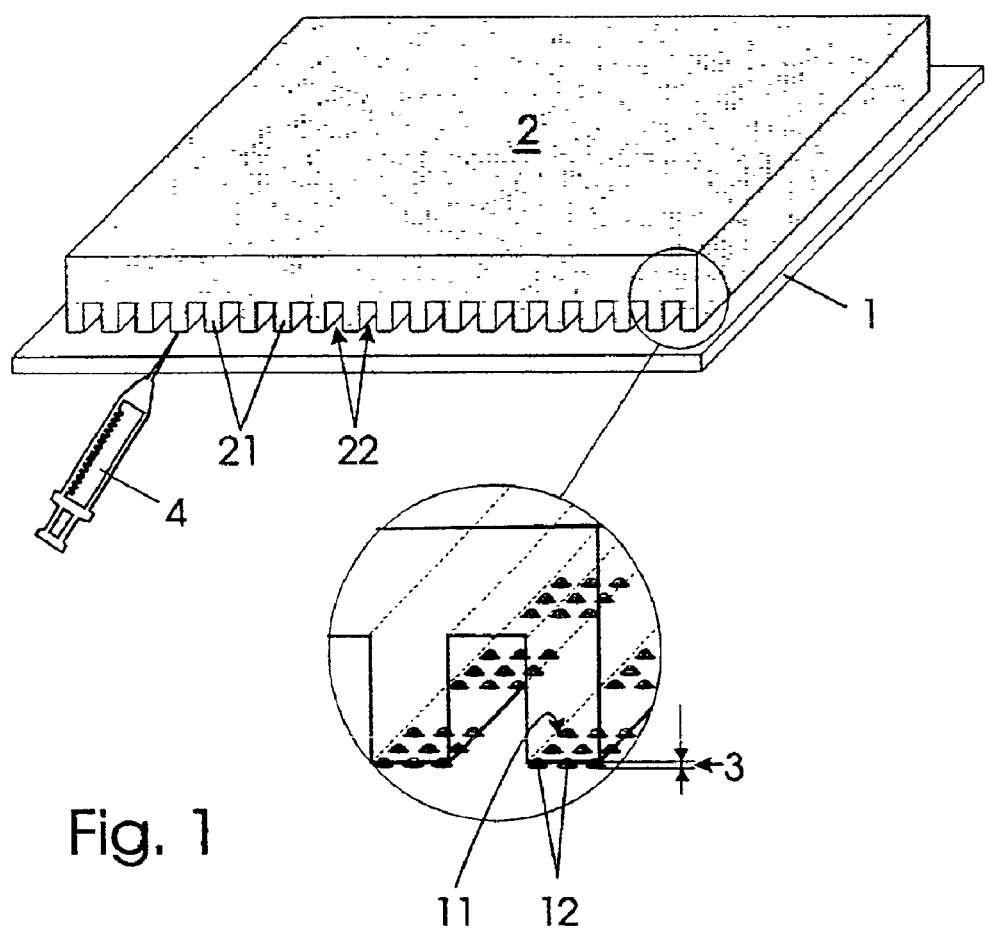

DEVICE FOR CARRYING OUT AN ALMOST SIMULTANEOUS SYNTHESIS OF A PLURALITY OF SAMPLES

BACKGROUND OF THE INVENTION

The invention relates to a device for a substantially simultaneous synthesis of a plurality of samples that are particularly for use in the automated laboratory work in the field of the combinatorial chemistry.

Sample particles, ("beads" or "Perlen"), have been used in separations and synthesis in the laboratory technical field for tenth of years. These particles mostly are glass or polymeric globules that have diameters of 0.01 mm up to 1 mm, typically about 0.1 mm, which are filled, dry or pre-swelled, as a loose material into a receptacle where they are then flushed by a liquid, whereby an adsorption process or a reaction process takes place between the solid phase surface of the particles and the liquid surrounding the particles. Methods of the column chromatography (for example, gel filtration), of the column extraction, of the immundiagnosis, of the bio-molecule purification (for example, DNA cleaning), as well as of the homogeneous and heterogeneous synthesis (of oligonucleotides, peptides or combinatorial substance libraries) utilize these techniques. In addition to the automation and miniaturizing of laboratory techniques, the parallelizing of the same is of great interest in obtaining a higher sample throughput and, hence, to speed up otherwise time-consuming procedures. To this end, samples are very often arranged in a raster so that the identity (origin, quality) of the sample can be associated to an area coordinate. Such coordinates are very easily to be detected in particular in automated systems of sample handling.

Therefore, so-called micro-titer plates have been developed for liquid samples, which support cavities in right-angular arrangements of 8·12 (96 samples) 16–24 (384) or 32·48 (1536). Thereby, the dimensions of the cavities of these sample holders depend on such volumes that can be reliably dosed by the commercially available devices (pipettes), and follow a miniaturizing continuously progressing with the dosing technology, what is simplified by the capability of an ali-quote (distribution of a mother-sample into different daughter-samples) of liquids at will.

Within the frame of work for miniaturizing laboratory procedures there is searched for possibilities to distribute sample particles, in analogy to the arrangement of liquid samples, in a two-dimensional raster. Since the miniaturizing of dosing liquids has already advanced very far, so the single particle becomes the smallest unit. Furthermore, there is the demand to handle high quantities, as it is common use when working with particles. 1-g polymer resin contains about 1 million particles.

There are different solutions known for filling micro-titer plates or reaction vessels.

So WO 98/24543 A1 describes a device for transferring liquids in which, inter alia, a micro-titer plate is provided, the chambers of which have at least one opening in their bottom area that is dimensioned in a way that, in the course of a filling operation, the passage of the liquid through this opening due to capillary forces is avoided. In WO 98/06490 A1 a device for an organic solid phase synthesis is described, in which the reaction vessel is arranged above a collective vessel for receiving liquids in such a way that the transfer of the liquid can be attained by generating a low pressure, whereas the liquid is held in the reaction vessel by a slight overpressure. From WO 97/19749 A1 there is a device for addressable combinatorial substance libraries known, in which one substance each is represented in a capillary tube, whereby the filling with liquids is obtained by capillary forces. In WO 97/37755 A1 a plate is described that contains a plurality of reaction cells being arranged in rows and columns, which are supplied with liquids by pumps. Furthermore, the specifications WO 97/43629 A1 and WO 98/16315 A1 describe distribution systems for liquids, which are comprised of a plurality of plates, whereby the liquid flow is operated and controlled by a capillary barrier and by electro-kinetic pumps, respectively.

The miniaturizing of the support plates mentioned goes along with the miniaturizing of the corresponding filling technologies and meets its critical geometric or time limits when conventional automated pipetting devices are used, since each single sample particle has to be supplied with liquids.

SUMMARY OF THE INVENTION

It is an object of the present invention to provide a device for a substantially simultaneous synthesis of a plurality of samples, which are bound to micro-beads provided in the cavities of a support plate.

The object is realized by the features of the first patent claim. Advantageous embodiments are covered by the dependent claims.

DETAILED DESCRIPTION OF THE INVENTION

Figures 2A, 2B:
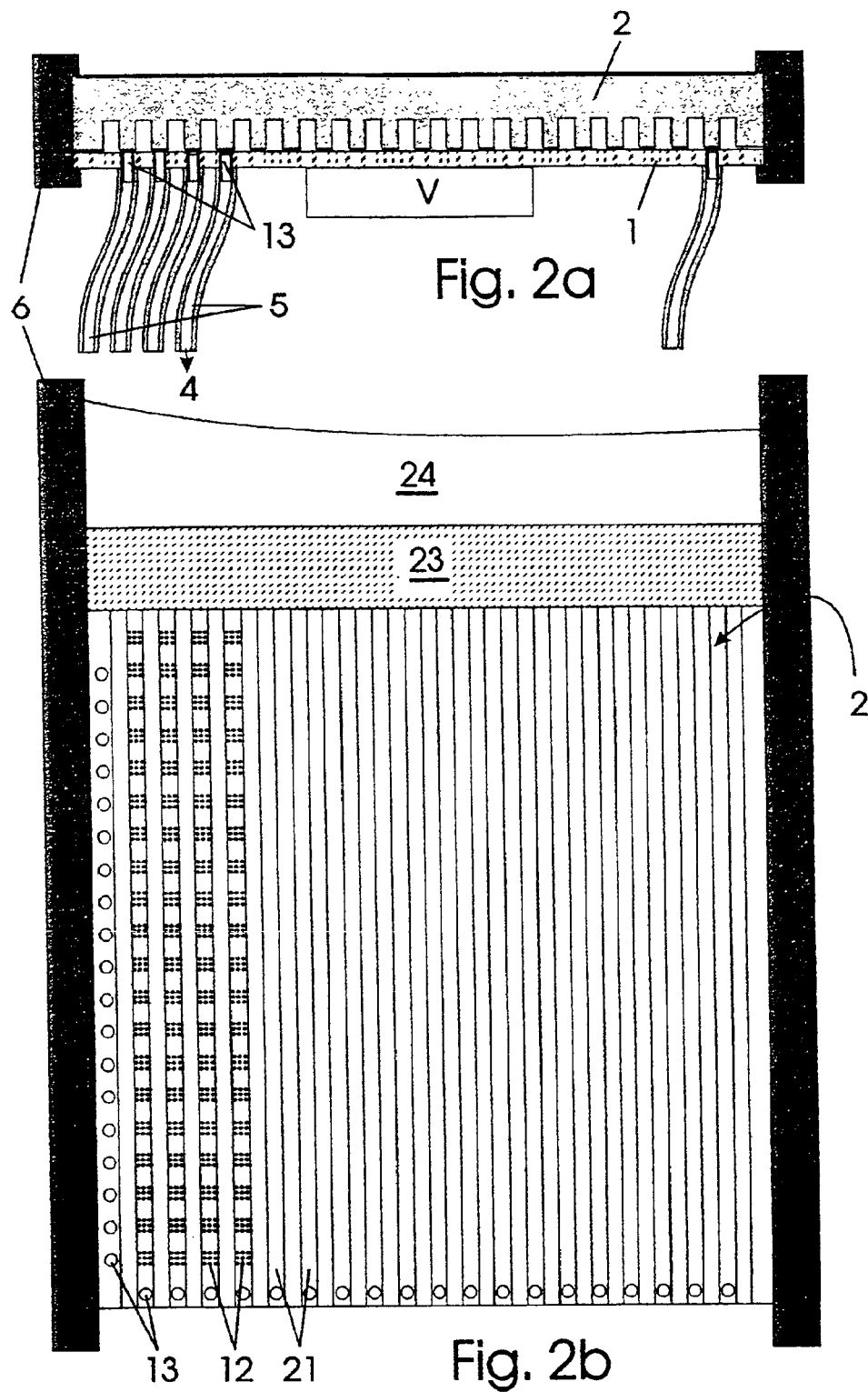
Figure 3:
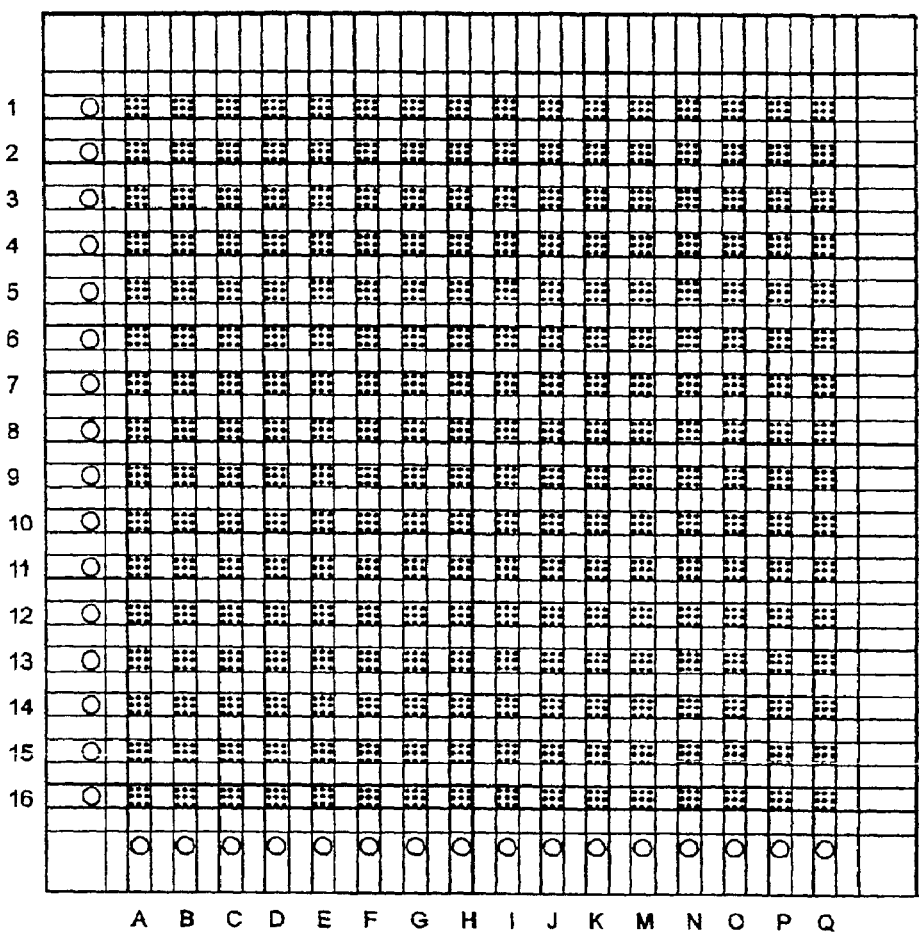
Figure 4:
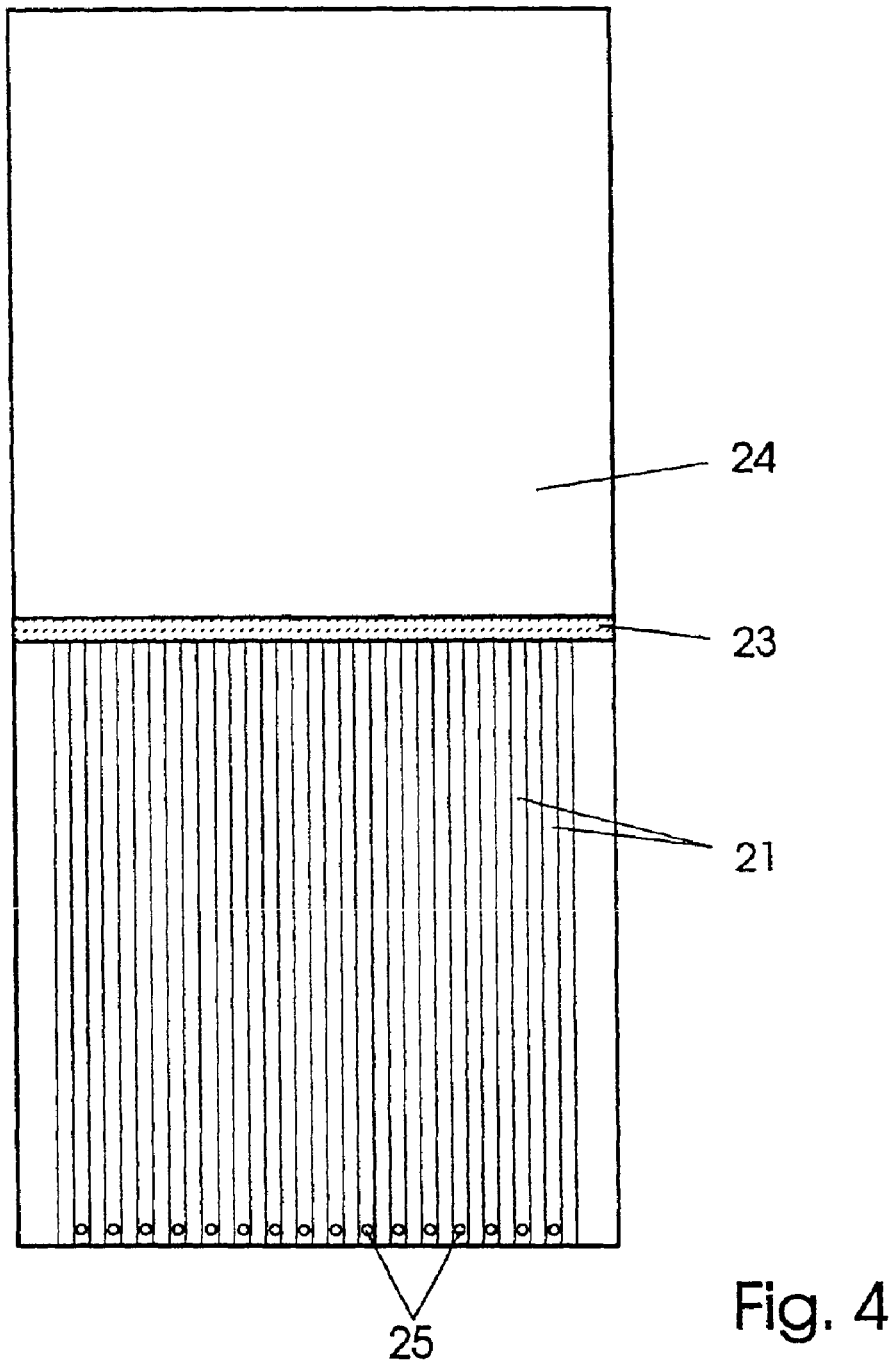

In the following, the invention will be explained in more detail by virtue of schematical embodiments. There is shown in:

FIG. 1 a perspective view of a principle setup of an inventional device as well as a representation of an enlarges detail;

FIG. 2a a lateral view of a device according to FIG. 1;

FIG. 2b a plan view of a device according to FIG. 1;

FIG. 3 a plan view of a device according to FIG. 1 with the position of an inventional cover in two synthesis steps; and FIG. 4 a plan view of an embodiment of a cover with a plurality of operational sections.

Without limiting the invention thereto, it will be started in FIG. 1 from a support plate 1, in which micro-beads 12 are provided in each of the single cavities 11 in such a way that the micro-beads project from out of these cavities. When micro-beads of a diameter of 100 $\mu$m are used, these micro-beads in the sorted-in state will project from out of the surface of the support plate 1 by of from 20 to 50 $\mu$m. In the present example, each nine of such micro-beads belong to one sample receiving area, whereby all the sample receiving areas are aligned to one another in rows and columns (refer to FIG. 3). A detachable cover 2 is provided above the bead-filled support plate 1, the cover 2 supports barriers 21 as most substantial elements. These barriers are so designed in their width and length that they capture all sample-receiving ranges of one row or column when attached to the support plate 1. In this manner, due to the definedly preselectable projecting of the micro-beads 12, a capillary gap 3 of preselectable height and of a defined width is produced, the latter by preselection of the width of the barriers 21. In a further arrangement of the micro-beads, for example, a plurality of set back micro-beads in a common cavity, such a capillary gap can be also formed in that the support plate 1 is provided with spacers of a defined height in the range, where the barriers 21 are supported, and/or the barriers 21 themselves are provided with spacers of a defined height.

In order to determine the sides of the capillary gaps 3, which are formed in this manner, the barriers 21 are spaced from one another by larger recesses 22, which are dimensioned in such a way that capillary forces will not be active any longer in these recesses.

The height of the capillary gap 3, at which the capillary forces will still be active in transporting liquids, depends on the surface tension of the material for the support plate 1 and for the barriers 21, and on the liquids that are to be handled. When materials such as glass and metal are used, between which a gap is formed, and water is used as a liquid, the capillary forces will be active up to gap heights of 500 $\mu$m. When using water, a specific hydrophilizing of the glass and/or of the metal surface permits the flowing of a liquid due to capillary forces also at greater distances. Depending on the synthesis fluid that is to be handled, the barriers 21 in the range of their supporting area on the support plate can be provided with a hydrophilic or hydrophobic surface, whereby at least the side walls of the recesses 22, which limit the barriers, should be provided with a respective oppositely acting surface covering.

The capillary gap, formed in the example by the projecting-out micro-beads 12, opens up the possibility to have liquids intentionally flow along the gap. Thereby a structurized cover plate is used for the cover 2 in the example, whereby this cover plate is provided with parallel recesses 22. By these recesses 22 a separation of two capillary gaps running in parallel to one another is obtained.

The capillary gaps will be filled in that a liquid is pipetted at the leading face of the cover, into a respective start of the gap, as is schematically indicated by way of a gap and by means of a dosable fluid dispenser 4 in FIG. 1.

The filling of each capillary gap with a different liquid requires a very careful pipetting of the liquids in order to prevent the mixing of two liquids. In order to ensure a simultaneous and equally dosed filling of all capillary gaps 3, it is more advantageous to provide the liquid supply via bores 13 in the support plate 1 or via bores 25 in the cover 2, which are respectively pre-positioned to a row and column of the cavities arranged in a line. A connection is provided via hose-like connections 5 or fitting pieces connected to these bores, to a liquid supply means, for example, a jet-pump, not shown in more detail in the following. This liquid supply means is associated to a respective row or column, whereby it is advantageous to apply a common and equally defined pressure to all liquid supplies. Such connections are adapted to feed now well-dosed liquids into the capillary gaps. It is, however, necessary to very precisely adapt the pumping rate of the jet-pump to the speed of flow of the liquid, produced by the capillary forces. This has to be detected by experiment for the individual case, in order to avoid a crossover of the liquid from a capillary gap to an adjacent one.

As already hinted at, it is also possible to realize the filling of the capillary gaps via the cover plate 2. Then the bores for the connections of the hoses have to be produced in the cover plate, centrally to the barriers 21. Such an embodiment also permits to use an adapter for a micro-titer plate instead of the hose connection, and to realize the filling of the capillary gaps by exploiting hydrostatic differences in pressure. One advantage in using jet-pumps connected to hose connections is the compactness of the system so that evaporations are avoided. Such a closed system is also advantageous in those cases where chemicals are used which must not get into contact with air.

The described modifications permit the filling of any desired number of lines with liquids. Presently, in adaptation to the micro-titer plates available, the described device permits the simultaneous filling of 96 lines. There are, however, no limits as to the number of lines, and with an increasing use of micro-technical machining processes there can be realized far more than 100 lines.

FIG. 2a shows an embodiment of the device according to FIG. 1 in a lateral front view, thereby the support plate 1 is provided with bores 13, only five of which are represented in FIG. 2a. Hose-like connections 5 are connected to these bores 13, said connections lead to not shown liquid supply means 4. The support plate 1, in turn, is mounted on a displacement table V, which enables a lateral displacement in parallel to the normal of the sheet. Furthermore, the support plate 1 and the cover 2 are connected to each other via a guiding means 6. Such a design permits to incorporate a further structurized cover 2, as it is shown in plan view in FIG. 2b in more detail. In addition to the transparent cover 2, described hereinbefore, including the barriers 21 provided to the same, the cover 2 further comprises a porous portion 23, which is followed by a plane section 24. The extensions of this plane section 24 are dimensioned in such a way that the plane section is capable of covering the entire support plate 1 under formation of a capillary gap capturing all the sample areas, provided that the covering range has been moved over the support plate 1. A complete design of only such a coverage alone is shown in FIG. 4, in which the bores 25, as an alternative, are there allocated to the first part of the cover 2.

Under use of the device described, the actual synthesis of the desired samples is performed as follows: The support plate 1, having a size of 250·250 mm2, which is filled with micro-beads 12 that, at a suitable porosity, can take, for example, a sample liquid volume of 0.25 nl, is brought into contact with the cover 2 containing the recesses 22. The support plate 1 and the cover 2 are aligned to each other by means of an adjustment device, not shown in detail, so that one projecting barrier 21 each rests upon a row of reaction chambers filled with beads. The barriers 21: connect, for example, one row with 96 sample fields that comprise 864 micro-beads 12. Moreover, the support plate in the example has two-times 96 through-bores 13 that lie in the extension of the rows and columns of the arrays of beads. The above-described hoses 5 are secured to these bores on the rear side of the support plate. The 192 hoses lead to the liquid supply means, for example syringes, which is, respectively, are filled with chemicals. A pressure is simultaneously applied to the syringes by a syringe drive, and the liquids are transported to the support plate 1 via the hoses 5. The capillary gaps 3 are filled with one chemical each. This is achieved in that the end of each barrier is placed accurately above one bore, from out of which the liquid is ejected for entering into the capillary gap. The pumping rate, which is controlled by the syringe drive, has to be correlated to the speed of flow of the liquids, driven by the capillary forces. A filling operation will take about 3 min., when a capillary gap of a height of about 30 $\mu$m, a width of about 1000 $\mu$m and a length of 250 mm is used.

The support plate 1 is mounted upon the displacement table V, which permits movements in parallel to the barriers 21, whereas the cover in the example should be safely arrested during the entire synthesis. Following the first synthesis step, the support plate I will be displaced underneath the cover 2 and along the barriers 21, in the course of which the micro-beads are conducted past by the porous portion 23 of the cover 2. Thereby the size of the pores in the porous portion has to be significantly smaller than the diameter of the micro-beads. The porous region absorbs the synthesis chemicals and these chemicals are drained from there by means of a device operating with low pressure and which is not represented in more detail; the micro-beads 12 are dried in this way. The support plate 1 is completely moved past below the porous area, until the entire support plate has arrived at the back end portion of the cover that is given a plane surface. In this section 24 the support plate 1 is subject to a rotation of 90°, which is necessary for performing the second synthesis step. Also in this case the support plate 1 is moved by means of a rotary table, while the cover remains safely clamped. After the support plate 1 has been rotated, the micro-synthesis beads are subject to a flushing. The flushing-out solution will also be transported by capillary forces to the beads. Again a drying of the beads is carried out by wiping over the porous portion 23 of the cover as described hereinabove. Then the cover 2 is again in a position for synthesis. The second synthesis step now proceeds in a same manner, the support plate 1, however, lies under the cover plate rotated by 90° and a further coupling step follows. There are further coupling steps possible, as many as desired. Thus, after the two-stage synthesis described, and starting from 96 rows and 96 columns, 9216 different combinations of twice 96 substances result. Further synthesis steps, after a respective rotation of the plates relative to each other, are feasible in any desired number. Two of the synthesis positions described are exemplified in FIG. 3 by example of sixteen rows (1 to 16) and sixteen columns (A to Q).

The use of borofloat glass for the cover 2 has proven as being particularly advantageous. In order to be able to visually supervise the liquid stream, which forms in the capillary channels mentioned, a transparent material should always be selected for the cover 2. Additionally, glass is distinguished by a high degree of flatness, which is is an important criterion for realizing a capillary gap of uniform thickness extending over a length of 250 mm. By use of diamnond cutting tools, 97 recesses 22 of a distance of 2.25 mm have been worked into a first range of the cover, under the condition that there are 96 rows and columns, respectively. The depth and width of a recess is so dimensioned that the recess 22 itself does not act like a capillary any more. To this end a width of 1000 $\mu$m and a depth of 1500 $\mu$m are selected in the embodiment described, thus barriers 21 of a width of 1.25 mm remain between two adjacent recesses. It lies within the scope of the invention to use other materials for the cover.

The design of the cover 2 described hereinabove is the most advantageous one, as concerns handling and stability of the device. It, however, also lies within the scope of the invention to realize the provided barriers by use of an arrangement of parallel stripes. To this end single stripes of glass are used correspondingly dimensioned in length and width. The height of the stripes can be selected as desired, and only depends on the stability requested from the device. The single stripes will be arranged parallel to each other at the distance of the sample receiving ranges, and they will be fixed relative to each other by sticking their ends onto a supporting stripe or to a support plate.

List of Reference Numerals
1—support plate
11—cavities
12—micro-beads
13,25—bores
2—cover
21—barriers
22—recesses (between the barriers 21)
23—porous portion
24—plane section
3—capillary gap
4—liquid supply means
5—connections (hoses)
6—guiding means

What is claimed is:

1. Device for a substantially simultaneous synthesis of a plurality of samples comprising a support plat having a plurality of cavities which, under formation of rows, are regularly arranged in a repeated raster, and which are adapted to receive micro-beads, wherein a detachable cover is provided, which has barriers of a defined width, said barriers cover and space apart at least one respective cavity associated to one row of cavities in such a manner that capillary gaps are formed between the micro-beads and the barriers, wherein the capillary gaps are formed by a space resulting from the micro-beads projecting from out of the cavities, with one dosageable liquid supply means being associated to each of said capillary gaps, and so large a recess remains between two respective adjacent barriers that said recess is capillary inactive.

2. Device as claimed in claim 1, wherein the cover is formed by a transparent plate, into which parallel indentations are inserted for formation of larger recesses.

3. Device as claimed in claim 1, wherein the barriers are provided with a hydrophilic or hydrophobic surface in the area where contacting the support plate, whereby at least the side walls of the recesses limiting the barriers are provided with a respective oppositely active surface coat.

4. Device as claimed in claim 1, wherein the support plate and the cover are mounted, by means of a guide, relative to each other in a connection which is laterally displaceable and rotatable by 90°.

5. Device as claimed in claim 4, wherein, subsequent to the barriers at least one porous portion and a further plane section are allocated to said cover, whereby said a further plane section covers the entire support plate.

6. Device as claimed in claim 1, wherein the liquid supply for the gaps takes place in the support plate via bores, each respective bore being pre-positioned to a respective row of cavities.

7. Device as claimed in claim 1, wherein the liquid supply for the gaps takes place in the cover via bores, each respective bore being pre-positioned to a respective row of cavities.

8. Device as claimed in claim 6 or 7, wherein said bores are provided with hose-like connections or fitting pieces, which are each connected to a liquid supply means, a defined pressure being adapted to be applied to said liquid supply means.

* * * * *